United States Patent [19]

Nelson et al.

[11] Patent Number: 4,787,750
[45] Date of Patent: Nov. 29, 1988

[54] GAS SPECTROMETER CONSTRUCTION HAVING AN IMPROVED ALIGNMENT FEATURE

[75] Inventors: Robert L. Nelson; William H. McIntyre, both of Orrville; William J. Danley, Green Township, Wayne County, all of Ohio

[73] Assignee: Westinghouse Electric Corp., Pittsburgh, Pa.

[21] Appl. No.: 35,835

[22] Filed: Apr. 8, 1987

[51] Int. Cl.$^4$ .................... G01N 21/15; G01N 21/31
[52] U.S. Cl. .................................... 356/437; 356/439
[58] Field of Search ............... 350/584, 358; 356/437, 356/438, 439, 45

[56] References Cited

U.S. PATENT DOCUMENTS

| | | | |
|---|---|---|---|
| 2,498,506 | 2/1950 | Ramser | 356/439 X |
| 4,422,154 | 12/1983 | Smithline et al. | 350/358 X |
| 4,657,386 | 4/1987 | Suarez-Gonzalez et al. | 356/45 |

OTHER PUBLICATIONS

Gottlieb et al., "Programmable Acousto-Optic Filter a Device for Multispectral Optical Processing", SPIE vol. 232, 1980, Int. Optical Computing Conf., (1980) pp. 33-41.

Primary Examiner—Vincent P. McGraw
Attorney, Agent, or Firm—G. E. Hawranko

[57] ABSTRACT

An across-the-stack gas analyzing spectrometer has a radiation source assembly including a cylindrical tube 22 having, in succession from its outer end toward the stack end a radiation emission assembly 28, a first lens assembly 30, and an AOTF assembly, all in optically aligned arrangement because of the circular perimeter of the elements in the circular tube, the arrangement also including a projecting second lens nozzle 98 received in an air window assembly 104 which forms a venturi with the second lens, the air window having a ball joint arrangement 120 for easy alignment of the directed beam, and also including a small diameter air window tube 142 through which clean air is directed into the stack through a larger diameter stack opening.

14 Claims, 3 Drawing Sheets

GAS SPECTROMETER CONSTRUCTION HAVING AN IMPROVED ALIGNMENT FEATURE

This invention pertains to the art of gas analyzing spectrometers and particularly to a construction arrangement of a radiation source assembly which, in its currently contemplated application, uses an acousto-optic tunable filter (AOTF) with an infrared emission source.

BACKGROUND OF THE INVENTION

The invention and its background are perhaps best understood in terms of what are considered to be drawbacks and problems posed by existing spectrometers of the across-the-stack type which "look" across a stack containing a gas of interest.

Stack analyzers using infrared, ultraviolet or visible radiation involve a series of optical elements normally mounted from and above a rigid, generally planar, mounting plate called an optical bench to provide a sturdy and stable mounting alignment between light source, mirrors, lenses and detector. Each optical element must be carefully aligned and stably secured to achieve proper operation. To obtain the required alignment generally requires careful machining and assembly.

Stack gas analyzers that look across the stack require a hole in the stack wall on each side of the stack to permit the transmission of radiation from a source on one side of the stack to a detector on the other side of the stack. To prevent escape of stack gases when the stack is under positive pressure, an element called an air window is usually incorporated in the analyzer and receives clean air under adequate positive pressure so that the air is forced into the stack to protect the analyzer from hot and dirty stack gases. A motor-operated slide valve or a weighted shutter is built into the horizontal duct which connects the analyzer to the stack. The valve or shutter is operated to a closed position in the event of loss of pressure of the clean air so that dirty stack gases cannot pass through the duct to analyzer elements. These valves or shutters in the horizontal duct are sometimes unreliable because of large bearing surfaces, dirt deposits, and excessive friction forces involved in their operation.

It is known to be desirable to maintain a negative or low pressure in the space adjacent the lens or window of the analyzer that interfaces with the stack gases to avoid the accumulation of dirt on the lens or window. This has been done by locating the lens in the low pressure region of a venturi throat in the flow path of the clean air supply through the air window element to the stack. Typically the arrangement to do this has included an annular flow passage in which the clean air flow first flows in a direction away from the stack to the venturi throat and then centrally into the stack. This arrangement inherently extends the length of the light path, which is not desirable.

When the light source and detector assemblies are mounted on opposite sides of the stack they must be aligned so that the source beam hits the detector after its passage through the stack. This either requires that the two stack holes and the analyzer mounting flange be in perfect alignment when they are prepared, which is difficult as a practical matter, or else some means of angle adjustment must be provided. One typical scheme for obtaining the angle adjustment utilizes a series of bellville washers between the analyzer flange and the adaptor flange to which the analyzer flange is connected. The numerous washers and parts involved make the adjustment difficult.

The air window element through which clean air is passed into the stack is intended to prevent the buildup of deposits in the duct part of the window which penetrates the stack so that the light beam is unimpeded. The larger the hole in the stack wall, the larger the volume of air flow of clean air is required to obtain velocities of the clean air sufficient to carry potential deposits out of the duct into the stack. Nevertheless a reasonably large hole is required to accommodate beam adjustment and aiming. These two conflicting requirements are considered to prevent optimization of the air lens design with current arrangements.

To provide stable AOTF operation at all ambient temperatures encountered in its location on the stack, it is desirable to maintain the AOTF at a constant temperature if possible. It is desirable that this be achieved by heating the filter to at least the highest temperature the filter is likely to see in normal operation and maintaining it at that temperature at all times, but without impeding the passage of light through the filter.

The radiation source intensity should be maintained at a constant level of radiation, consume as little power as possible and conduct as little heat as possible to the AOTF. Most analyzers of which we are aware have a source that is exposed to the convective currents and dissipate energy by thermal loss so that source radiation varies. The source and lens are also usually exposed to the atmosphere and thus subject to contamination. Additionally, the AOTF material may be subject to oxidation.

The aim of this invention is to provide a spectrometer design having a radiation and source assembly construction and arrangement which provides solutions to these problems and drawbacks of the typical existing spectrometers.

SUMMARY OF THE INVENTION

With this aim in mind, and in accordance with the invention, there is provided for an across-the-stack gas analyzing spectrometer of the type including a gas detector assembly on one side of the stack, and a radiation source assembly on the opposite side of the stack, with a stack opening associated with each assembly to permit the transmission of radiation therebetween, various improvements of said radiation source assembly including, among others, the provision of a cylindrical tube containing, in succession from the outer end toward the stack end, a radiation emitting assembly, a first lens assembly, and an acousto-optic tunable filter assembly in optically aligned relation.

Another aspect of the invention includes the improvement comprising an air window assembly means connecting the radiation source of detector assembly to said stack and including a hollow central core part through which clean air from an external source is passed into said stack to prevent flow of contaminated gas from said stack toward said source or detector assembly, and air window tube means receiving said clean air, of substantially smaller diameter than said stack opening, so as to provide annular space therebetween, extending into said stack opening from said air window assembly means, and said air window tube means includes opening means therein to direct air into said annular space between said tube and stack opening to reduce contaminant-buildup in said annular space.

Addition features of the invention will be explained in the Description of the Preferred Embodiment.

DESCRIPTION OF THE PREFERRED EMBODIMENT

Figure 1:
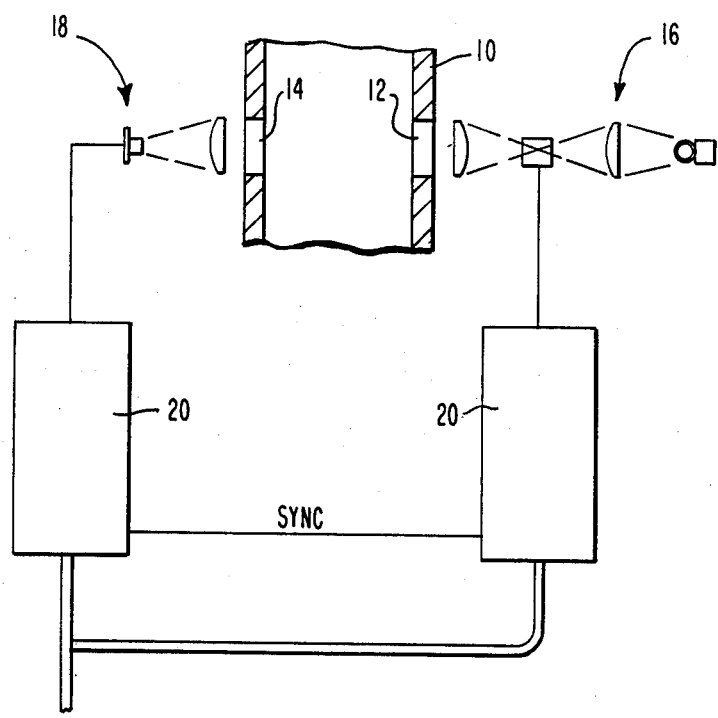
FIG. 1 is a generally schematic view of an overall stack gas analyzer design adapted to use the arrangement of the invention.

Referring to FIG. 1, the general arrangement in which the invention can be used is shown schematically. A stack 10, or other conduit through which gases of interest pass, has opposite openings 12 and 14 through which radiation is passed from a radiation source assembly according to the invention and generally designated 16 on the right side of the stack in FIG. 1, to a detector assembly generally designated 18 on the left side. This type of gas analyzing spectrometer is herein characterized as an across-the-stack type although it will be appreciated that the "stack" may be any conduit through which gases of interest pass.

The optical system, which comprises the source and detector assemblies 16 and 18 respectively, are both electrically connected to a stack mounted electronics system 20 which in turn is connected to a control room electronic system (not shown), neither of the latter systems comprising any part of this invention.

The overall arrangement of source and detector assemblies and the stack mounted electronics system is disclosed in detail in U.S. Pat. No. 4,652,756, issued to F. M. Ryan et al. on Mar. 27, 1987, and a currently preferred detector assembly is disclosed in detail in U.S. Pat. No. 4,736,103 issued to R. L. Nelson et al. on Apr. 5, 1988, both patents being owned by the assignee of this application. Reference should be had to these patents for information on details therein which are not here treated since not considered a part of this invention.

Figure 2:
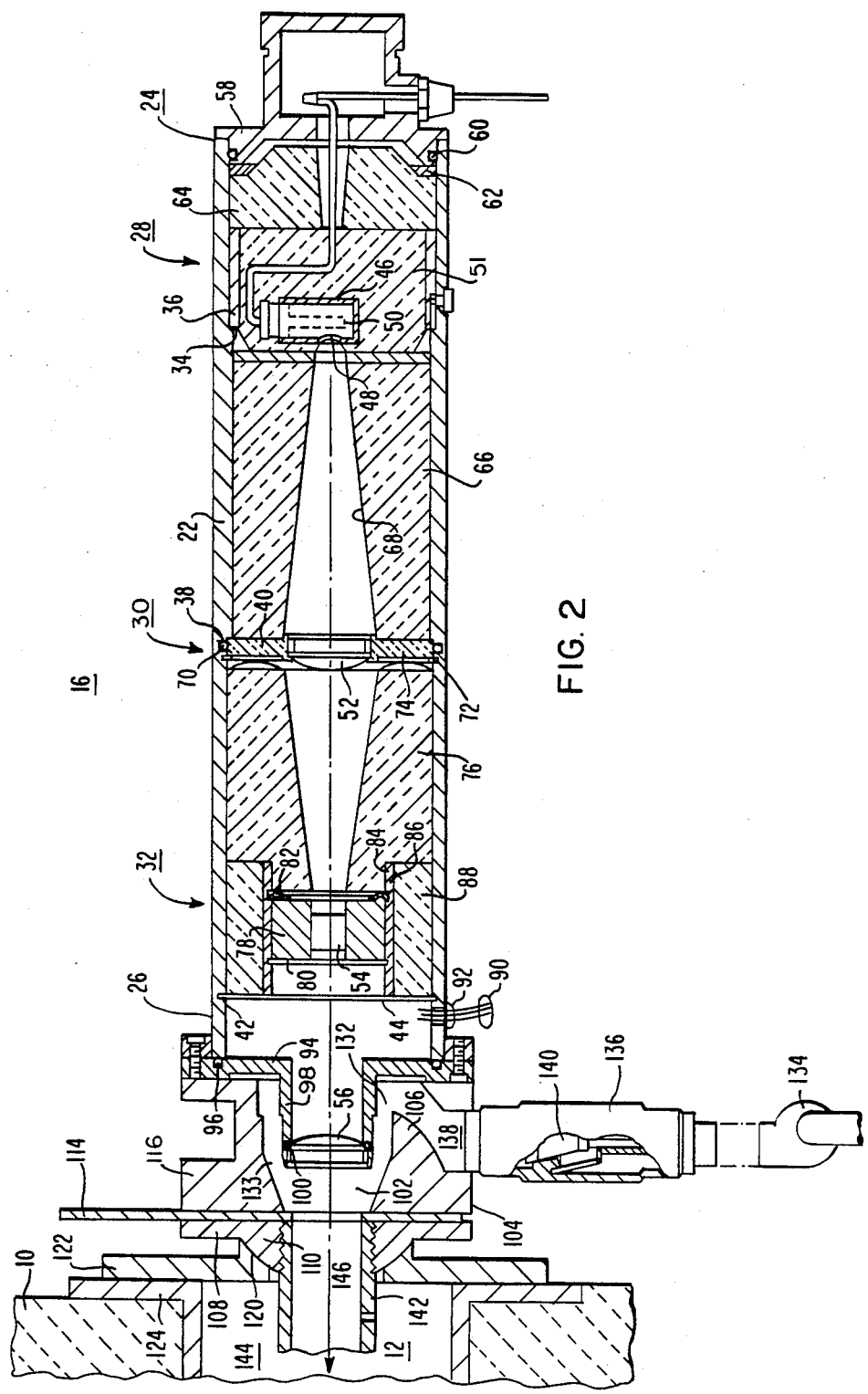
FIG. 2 is a view in the nature of a vertical cross-section illustrating a radiation source assembly having an arrangement according to the invention.

The radiation source assembly generally designated 16 in FIG. 2 provides a construction arrangement in which a major feature is the provision of a cylindrical tube 22 providing a stiff, inexpensive, high tolerance element serving in itself as the optical bench. The tube 22 houses, in succession from the outer end 24 of the tube toward the stack end 26 of the tube a radiation emitting assembly generally designated 28, a first lens assembly generally designated 30 and an acousto-optic tunable filter (AOTF) assembly 32, all of which are disposed in the tube in optically aligned relation. Each of these assemblies 28–32 includes a mounting which has a circular periphery so that as each is received within the tube, it self-aligns. The currently preferred tube 22 material is aluminum which can easily be machined internally to high tolerances. An internal shoulder 34 is machined toward the outer end of the tube to provide for an abutment seat for the peripheral element 36 of the emission assembly. Another shoulder 38 is formed to provide a seat against which the mounting disk 40 of the first lens assembly abuts. An internal groove 42 is formed near the stack end 26 of the tube to receive an internal snap ring 44 which also functions as shoulder means for the AOTF assembly.

The radiation emitting assembly 28 includes, besides the peripheral sleeve 36, a cylindrical shell 46 with an opening 48 therein through which the radiation from the source 50 is emitted. The interior of the shell 46 reflects radiation back onto the source itself except for that which is emitted through the hole 48 in the shell, this radiation being directed toward the AOTF. The shell 46 is encased in a stiff thermal insulation block 51 to reduce conductive losses to the atmosphere and to the AOTF mount. The completely enclosed nature of the source prevents convection losses as well. While the cylindrical shell of the emitting assembly is shown disposed with its longitudinal axis at a right angle to the axis of the tube 22, it is within the contemplation of the invention that the longitudinal axis of the shell be aligned generally with the longitudinal axis of the tube with an open end of the shell facing the stack. In this case the emitter source part can be in the form of a separable element which can be removed from the reflecting cylinder and out the outer end 24 of the tube for service purposes.

the source 50 provides infrared radiation of a broad band character. Which is directed through the lens 52 of the first lens assembly 30 and through the AOTF in which a narrow bandwidth portion of the radiation is selected and distinguished from the remaining infrared radiation through the operation of an rf transducer (not shown) and then through the second lens 56 and into the stack 10. The operating principles of the AOTF 54 are known and further information relative thereto may be found in the first noted patent application and references therein.

The outer end 24 of the cylindrical tube 22 is provided with an end cap 58 which is in sealed relation to the interior of the tube through the provision of an o-ring seal 60. Wavy ring washer means 62 urges the stiff insulation block 64 against stiff insulation block 51 of the radiation emitting assembly 28 to insure proper seating of the sleeve 36 against the shoulder 34 of the tube 22.

Another stiff insulation block 66 with a diverging bore 68 occupies the space between the emission assembly 28 and the first lens assembly 30. An o-ring seal 70 is provided at the periphery of the lens assembly disk 40 and an internal snap ring 72 holds the disk 40 firmly seated against the shoulder 38 of the tube. A wavy ring 74 urges another thermal insulation block 76 to the left to bear against parts of the AOTF assembly which in turn is retained against leftward movement by the snap ring 44.

The AOTF assembly 32 includes the AOTF 54 mounted in a metallic block 78 which is retained in place by a snap ring 80 at one face of the block and a wavy ring washer 82 at the other face of the block. The ring and washer are received in grooves in a metallic filter mount spool piece 84 which has a film type heater 86 around its outer circumferential face and is encompassed by thermal insulation 88 around the barrel of the spool piece. This arrangement permits simple removal of the entire AOTF assembly as a discrete subassembly, and the removal and replacement does not disturb the concentric alignment assured by the cylindrical construction.

Electric power is provided through leads 90 entering the tube through a hermetic seal at 92. These leads provide rf power to the transducer of the AOTF, power to the heater 86, and also include thermocouple means for measuring the temperature of the AOTF and the heater. This arrangement permits constant temperature control of the AOTF at a temperature in excess of that which would be expected without the use of a heater, irrespective of variations in ambient temperature about the spectrometer, such constant temperature control promoting accuracy over a wide range of ambient conditions.

The stack end of the cylindrical tube is sealed by second cap means 94 connected to the tube, with an o-ring seal 96 between cap and tube. The second cap means includes a centered lens nozzle 98 projecting toward the stack opening and having the second lens assembly 56 adjacent the stack end of the nozzle and in sealed relation with the nozzle 98 through o-ring seal 100. The lens nozzle projects into the hollow central core part 102 of the air window assembly means generally designated 104 which is secured to the end cap 94 and tube 22.

Figure 3:
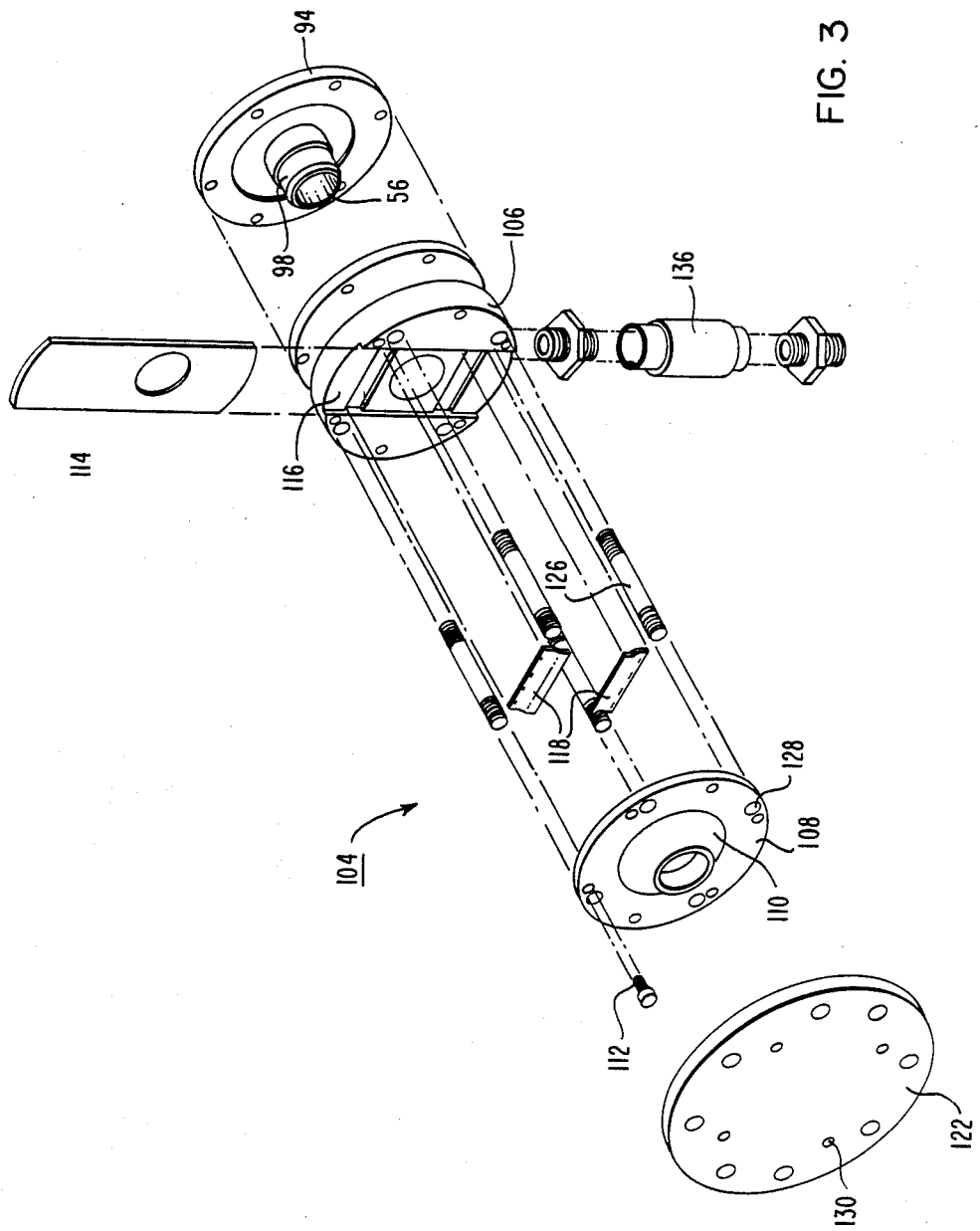
FIG. 3 is an exploded isometric view showing the major parts of an air window assembly according to the invention.

The air window assembly 104 (FIGS. 2 and 3) includes a body part 106 to which a plate 108 having a spherical or ball joint protrusion 110 is secured by fasteners 112 threaded into the body part. A manual shutter 114 is sandwiched between the body 106 and ball joint plate 108 in a relieved part 116 of the body. A pair of leaf springs 118 are secured in the relieved part 116 to seal against undue air leakage along the shutter.

The convex part 110 of the ball joint fits in a concave seat 120 which is a part of the plate 122 which in turn is fastened to the flange 124 of the member defining the opening 12 in the stack.

To fasten the body part 106 and plate 108 to the seating plate 122, a series of studs 126 are inserted through a corresponding series of oversize holes 128 in the plate 108 and threaded into openings 130 in the seating plate 122. The body part 106 is then fitted over the projecting studs 126 and nuts (not shown) are tightened down on the studs 126 to complete the air window assembly as a discrete subassembly. The air window assembly is then fastened to the second end cap 94. To align the direct beam with the detector element on the opposite side of the stack, through the adjustment of the spherical joint arrangement, the nuts on the ends of the studs 126 are loosened sufficiently to accommodate relative movement of the ball joint part 110 with the seat 120 and when the alignment is that desired the nuts are tightened.

Referring particularly to FIG. 2, as noted before the air window body 106 has a hollow core portion 102 which provides an annular space 132 around the lens nozzle 94, with the hollow core narrowing toward the stack. This arrangement effectively forms a venturi throat 133 adjacent the stack end of the lens nozzle to aid in keeping the face in lens 56 clean.

Air flow for the air window assembly is provided from a clean air source 134 to a check valve 136 connected to the opening 138 in the air window assembly. The check valve 136 preferably includes a gravity operated valve element 140 which opens in response to air flow and closes in response to the absence of air flow. The clean air flow is through the annular space 312, the venturi throat 133 and then through an air window tube 142 which, as shown in FIG. 2, may conveniently be threaded into the one side 120 of the spherical joint. The air window tube 142 has a diameter substantially smaller than the diameter of the stack opening so as to provide an annular space 144 around the air window tube. The air window tube also includes openings 146 in its wall to cause some of the air through the tube to be directed through the openings 146 to reduce contaminant buildup from the stack in the annular space 144. A substantial buildup of contaminants in this annular space 144 could prevent easy movement of the air window tube 142 during the step of aligning the beam by adjustment of the ball joint.

The size of the fan 134 or other device for furnishing clean air is determined in accordance with the resistance losses in the passage into the stack, relative to the pressure of the dirty gases in the stack, to provide adequate air flow to keep the opening 12 relatively clear and prevent back flow of dirty gases into the air window assembly.

In the event of loss of air pressure from fan 134, the check valve 136 will close to prevent flow of dirty gas back toward the air source. The air window assembly is also equipped with sensing means (not shown) to determine when the clean air source pressure is lost so that the operators can be alerted to this condition.

Some of the more salient features of the arrangement provided by the construction will now be noted. The simple vertically mounted gravity actuated check valve 136 is installed between the blower and the air window assembly, rather than between the stack opening and the air window, the result of this is that moving valve element 140 is farther away from the stack and therefore less likely to be subject to the high temperature associated with the stack. Further very low friction forces are involved in a vertical check valve so that high reliability can be achieved. The manually operated shutter 114 provides the function of isolating the analyzer from stack gases the same as the prior art shutter or valve noted before, but is simpler and more reliable through manual operation.

The provision in the arrangement of the lens being built into the nozzle 98 integral with the radiation source assembly as a whole, and the provision of providing the venturi throat between the air window body and the nozzle, allows the lens 56 to be located closer to the stack, thus shortening the total length of the source assembly while still maintaining the lens 52 to AOTF 54 to lens 56 distance required with an AOTF.

The provision of the ball joint permits alignment adjustment of up to 15 degrees so that perfect alignment can be achieved even though the stack flanges are somewhat out of alignment.

The air window tube 142 is directly connected to the analyzer side of the ball joint so that the tube may be directed at the detector across the stack. The use of a window tube substantially smaller in diameter than the stack opening also minimizes the air flow required to achieve the desired air window effect since the velocity is higher for a given air flow than would be obtained if the hole in the stack were to serve as the air window. This essentially assures that the tube will remain clear with a minimum of air flow.

The air window assembly including the tube 142 can also be connected to detector assembly 16 to function in the same way as has been described in connection with the source assembly 16.

I claim:

1. For an across-the-stack gas analyzing spectrometer of the type including a gas detector assembly on one side of the stack, and a radiation source assembly on the opposite side of the stack, with a stack opening associated with each assembly to permit the transmission of radiation therebetween, the improvement of said radiation source assembly comprising:

a cylindrical tube housing, in succession from the outer end toward the stack end, a radiation emitting assembly, a first lens assembly, and an acousto optic tunable filter (AOTF) assembly in optically aligned relation;

a first cap means on said outer end of said tube;

a second cap means on said stack end of said tube including a centered lens nozzle projecting toward said stack opening;

air window assembly means including a cylindrical body part having a hollow central core part accommodating said lens nozzle with a first annular space around said nozzle; and spherical joint means between said air window assembly means and said stack to accommodate aligning said radiation source assembly with said detector assembly across said stack.

2. The improved source assembly of claim 1 including:

shoulder means internally of said tube associated with each of said succession of assemblies; and means biasing each of said succession of assemblies into seating relation with its respective shoulder.

3. The improved source assembly of claim 1 including:

said second cap means having a second lens assembly adjacent the stack end of said nozzle;

said core part of said air window assembly means narrowing toward said stack; and means for delivering air from a clean air source to said first annular space to flow past said lens nozzle to said stack opening.

4. The improved source assembly of claim 3 wherein:

said narrowing core part forms a venturi throat with said lens nozzle adjacent said second lens assembly.

5. The improved source assembly of claim 1 wherein:

said air window assembly means is detachably secured to said second cap means to permit, when said air window assembly is detached, ready access to said second lens assembly.

6. The improved source assembly of claim 1 wherein:

said first and second cap means include seal means associated therewith; and each of said first and second lens assemblies includes seal means to provide separate, sealed chambers in said cylindrical tube to accommodate gas purging and sealing.

7. The improved source assembly of claim 1 wherein:

said radiation emitting assembly includes a reflecting, cylindrical shell having an opening therein for the emission of radiation, said cylindrical shell being mounted in a thermal insulation block to reduce losses from said radiation source.

8. The improved source assembly of claim 1 wherein:

said AOTF assembly includes thermal insulation and heater means encompassing said AOTF and forming a discrete subassembly removable from, and replaceable in, said cylindrical tube.

9. The improved source assembly of claim 1 including:

air window tube means, of small diameter than said stack opening, so as to provide a second annular space therebetween, extending into said stack opening from said spherical joint.

10. The improved source assembly of claim 9 wherein:

said air window tube means includes opening means therein to direct air into said second annular space between said tube and stack opening to reduce contaminant build-up in said second annular space.

11. The improved source assembly of claim 1 including:

check valve means between said clean air source and said first annular space.

12. The improved source assembly of claim 11 wherein:

said check valve means includes a gravity-biased valve operable to a closed position in response to failure of air flow from said air source.

13. The improved source assembly of claim 11 including:

manually operable shutter means selectively operable to block communication between said stack opening and said hollow central core part.

14. For an across-the-stack gas analyzing spectrometer of the type including a gas detector assembly on one side of the stack, and a radiation source assembly on the opposite side of the stack, with a stack opening associated with each assembly to permit the transmission of radiation therebetween, and having:

air window assembly means connecting at least one of said radiation source and detector assemblies to said stack and including a hollow central core part through which clean air from an external source is passed into said stack to prevent flow of contaminated gas from aid stack toward said source or detector assembly, the improvement comprising:

air window tube means, of substantially smaller diameter than said stack opening, so as to provide an annular space therebetween, extending into said stack opening from said air widow assembly means;

said air window tube means includes opening means therein to direct air into said annular space between said tube and stack opening to reduce contaminant build-up in said annular space; and spherical joint means between said air window assembly means and said stack to accommodate aligning said radiation source assembly with said detector assembly across said stack.

* * * * *